(12) United States Patent
Nallakrishnan

(10) Patent No.: US 8,845,574 B2  
(45) Date of Patent: Sep. 30, 2014

(54) WEIGHTED INFUSION SLEEVE

(75) Inventor: Ravi Nallakrishnan, Westmont, IL (US)

(73) Assignee: Art, Limited, Grand Cayman (KY)

( * ) Notice: Subject to any disclaimer, the term of this patent is extended or adjusted under 35 U.S.C. 154(b) by 207 days.

(21) Appl. No.: 13/031,074

(22) Filed: Feb. 18, 2011

(65) Prior Publication Data

US 2011/0201995 A1 Aug. 18, 2011

Related U.S. Application Data

(60) Provisional application No. 61/305,887, filed on Feb. 18, 2010.

(51) Int. Cl.  
*A61B 17/20* (2006.01)  
*A61F 9/007* (2006.01)

(52) U.S. Cl.  
CPC .................................. *A61F 9/00736* (2013.01)  
USPC ............................................ 604/22; 604/264

(58) Field of Classification Search  
USPC .................... 604/22, 521, 264, 272  
See application file for complete search history.

(56) References Cited

U.S. PATENT DOCUMENTS

| | | | | |
|---|---|---|---|---|
| 5,643,298 | A | * | 7/1997 | Nordgren et al. ............. 606/159 |
| 5,685,841 | A | * | 11/1997 | Mackool ......................... 604/22 |
| 6,605,054 | B2 | * | 8/2003 | Rockley .......................... 604/22 |
| 2006/0100653 | A1 | * | 5/2006 | Akahoshi ...................... 606/169 |

* cited by examiner

*Primary Examiner* — Kami A Bosworth  
*Assistant Examiner* — Glen Janson  
(74) *Attorney, Agent, or Firm* — Wood, Phillips, Katz, Clark & Mortimer

(57) ABSTRACT

An irrigation sleeve for a phacoemulsification needle is constructed with a non-uniform distribution of mass. When the sleeve is used with torsional phacoemulsification apparatus the sleeve adds to the eccentric motion of the needle, adding efficiency to the phacoemulsification process. In one embodiment, weights are implanted in the sleeve. In another embodiment the sleeve is molded with concentrations of sleeve material at selected locations in the sleeve.

9 Claims, 4 Drawing Sheets

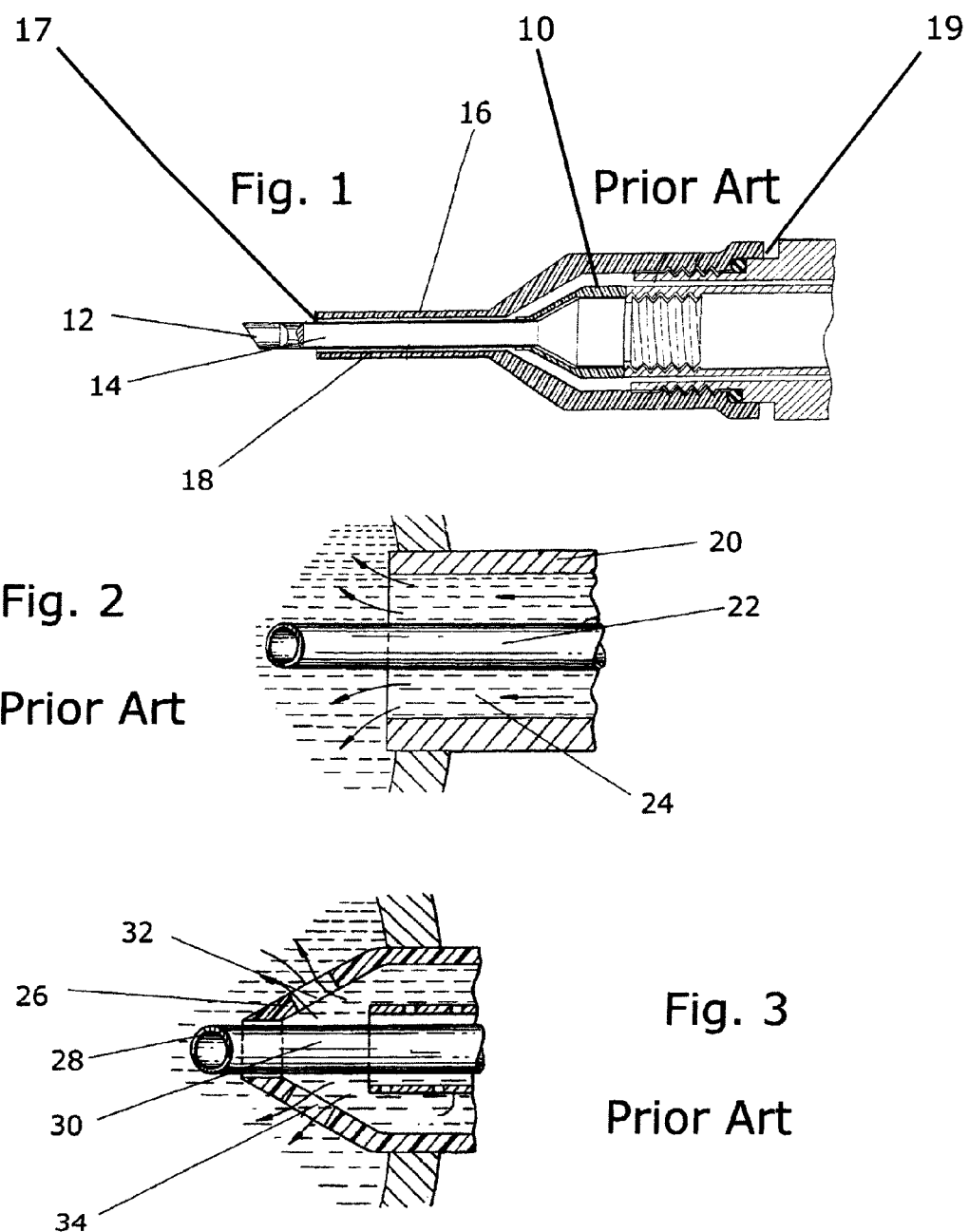

WEIGHTED INFUSION SLEEVE

This application claims priority from U.S. patent application Ser. No. 61/305,887, filed Feb. 18, 2010 and entitled "Weighted Infusion Sleeve" which is incorporated herein in its entirety.

BACKGROUND OF THE INVENTION

The present invention relates to surgical instruments and surgical techniques used in eye surgery and, more particularly, to an infusion sleeve for use with a phacoemulsification needle.

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such technique is known as phacoemulsification. A typical phacoemulsification surgical instrument includes a hollow phacoemulsification needle attached to a hand piece. The hand piece is adapted to vibrate the needle at ultrasonic frequencies in order to fragment the diseased lens into particles small enough to be aspirated from the eye through the needle.

Commonly, an infusion sleeve is mounted around the needle to supply irrigating liquid to the eye in order to aid in flushing and aspirating lens particles and to maintain adequate intraocular pressure within the eye during the procedure.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small in incision as possible during such surgery is the minimization of leakage of liquid during and after surgery and the prevention of such a collapse When first developed, phacoemulsification involved vibrating the needle in a longitudinal direction with respect to the handpiece. Changes in techniques and equipment now provide for vibration of the needle in a number of different modes in which the needle is moved not only longitudinally but in a side-to-side, torsional or eccentric motion. As hand pieces have been developed to provide these motions, needles themselves have been manufactured which heighten the eccentric motion created by the hand piece.

Instruments using various types of infusing sleeves are well known and well-represented in the art and exemplify the attempts made by others to address the problem of maintaining an adequate flow of irrigating liquid without causing damage to the eye.

U.S. Pat. No. 4,643,717 (Cook et al) teaches and describes an aspiration fitting adapter formed as a sleeve concentric to the phaco needle and having a pair of bilaterally opposed discharge ports formed proximate the end of the sleeve to infuse irrigating liquid into the eye.

U.S. Pat. No. 5,151,084 (Khek) teaches and describes an ultrasonic needle with an infusion sleeve that includes a baffle. The sleeve of Khek also fits concentrically about the needle and allows the needle to protrude a substantial distance therefrom while providing pair of discharge ports bilaterally opposed to each other near the terminus of the sleeve.

U.S. Pat. No. 6,117,151 (Urich et al) teaches and describes an eye incision temperature protection sleeve fitted concentrically about a needle and having a single discharge port through which irrigating liquid is passed.

U.S. Pat. No. 6,605,054 (Rockley) teaches and describes a multiple bypass port phaco tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

A series of patents issued to Richard J. Mackool illustrates further variations of irrigating sleeves. Mackool forms the sleeve with a somewhat flattened cross-section configuration intended to more closely approximate the shape of the incision through which the sleeve is inserted into the eye. This cross-section can be seen at FIG. 3 of U.S. Pat. No. 5,084,009.

U.S. Pat. No. 5,084,009 (Mackool) teaches and describes a liquid infusion sleeve for use during eye surgery with the sleeve having a flattened cross-section and having a pair of infusion ports formed on the forward portion of the flattened section.

U.S. Pat. No. 5,286,256 (Mackool) teaches and describes a liquid infusion sleeve having a free-floating rigid sleeve surrounding a needle which is intended to prevent the outer flexible sleeve from collapsing onto the needle.

U.S. Pat. No. 5,354,265 (Mackool) teaches and describes a liquid infusion sleeve showing yet another construction intended to keep the outer flexible infusion sleeve from collapsing onto the vibrating needle.

U.S. Pat. No. 5,505,693 (Mackool) teaches and describes a method and apparatus for reducing friction and heat generation by an ultrasonic device during surgery incorporating a needle support to prevent collapse of the outer flexible sleeve.

The Mackool patents are characterized by a pair of discharge ports formed at the distal end of the sleeve through which irrigating liquid is passed into the eye during the operation.

U.S. Pat. No. 5,645,530 (Boukhny) teaches and describes a phaco emulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

U.S. Pat. No. 5,634,912 (Injev) teaches and describes an infusion sleeve having a rotating tip to allow the phaco needle to be repositioned during surgery. The top also has a single discharge port for infusing liquid during surgery.

Published U.S. Patent Application No. 2003/0004455 (Kadziauskas) teaches and describes a bi-manual phaco needle using separate emulsification and aspiration needles inserted into the eye simultaneously during surgery.

While the foregoing references describe a variety of phacoemulsification needles and sleeves, they do not particularly point out nor describe the aspects of the present invention which include manufacturing an infusion sleeve which will add its own contribution to the eccentric motion produced by a hand piece and needle combination. Accordingly, a need exists for an improved infusion sleeve which is constructed in a manner that adds a component of eccentric motion to a phacoemulsification needle and hand piece combination.

The need also exists for such improved infusion sleeves to be simple in construction, efficient in operation and economical to manufacture.

In accordance with the preferred embodiment of the present invention, a phacoemulsification infusion sleeve is manufactured with a non-uniform distribution of material which causes the sleeve to add an element of eccentric motion to the phacoemulsification needle. In one version, weights are included at selected locations within the infusion sleeve to cause the infusion sleeve to be asymmetrically balanced.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

These and further aspects of the present invention will become apparent upon consideration of the accompanying drawing figures in which:

BRIEF DESCRIPTION OF THE DRAWINGS

FIG. 1 is a first prior art illustration of a prior art irrigation sleeve;

FIG. 2 is a second illustration of a prior art irrigation sleeve;

FIG. 3 is a third illustration of a prior art irrigation sleeve;

DETAILED DESCRIPTION OF THE DRAWINGS

Figure 4:
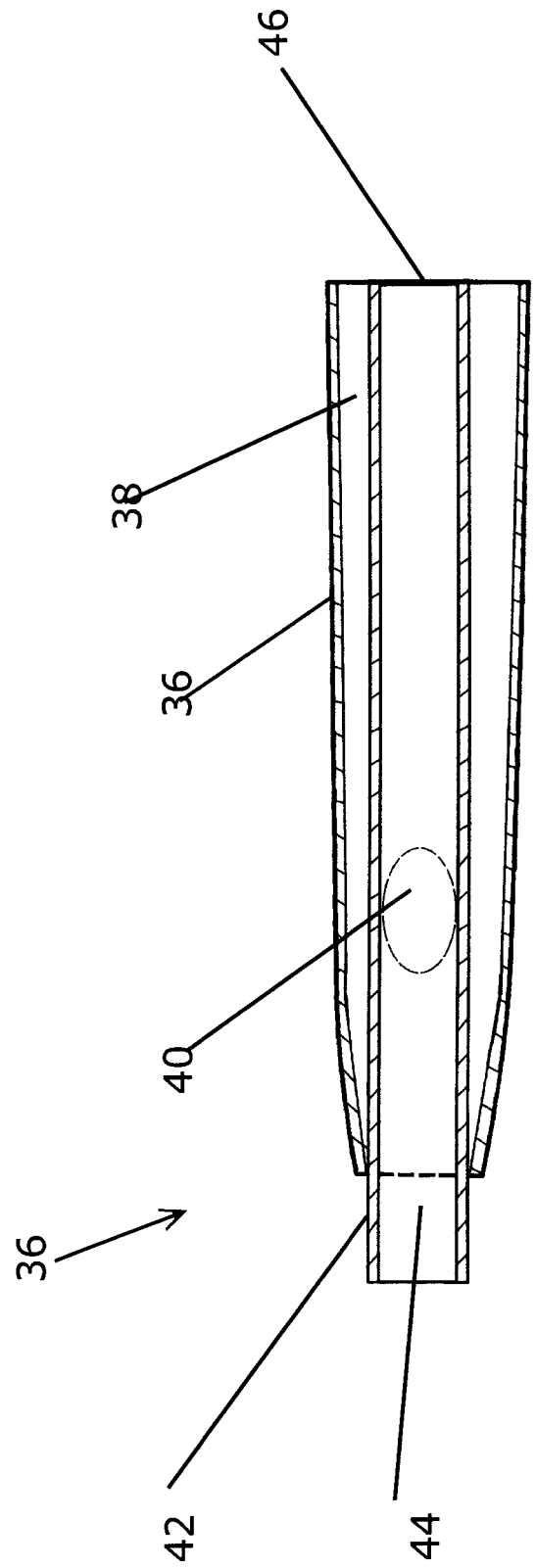
FIG. 4 is a sectional view of a prior art infusion sleeve attached to a phacoemulsification needle.

Referring now to FIG. 1 the numeral 10 indicates generally a partial sectional view of a prior art phacoemulsification hand piece having a needle 12 defining a hollow internal chamber 14 through which irrigation liquid and emulsified particles of a lens are aspirated from the capsular bag. As seen in FIGS. 1 and 2, an irrigating sleeve 16 from which needle 12 protrudes at sleeve distal end 17 is mounted to hand piece 10, at sleeve proximal end 19. Sleeve 16 communicates with an irrigation liquid supply within handpiece 10 and provides irrigating liquid to the capsular bag through an annular channel 18 formed between needle 12 and sleeve 16.

Referring now to FIG. 2, an enlarged partial sectional view of a second prior art phacoemulsification apparatus is shown having a sleeve 20 surrounding a hollow needle 22 and defining therebetween an annular channel 24 as a conduit for irrigating liquid.

Both FIG. 1 and FIG. 2 show a prior art apparatus with the flow of irrigating liquid directed annularly about the periphery of the hollow phaco needle with the space available for flow being fixed in size.

Referring now to FIG. 3, a partial sectional view of a second embodiment of the apparatus of FIG. 2 is shown where the infusion sleeve 26 tapers to form an opening 28 through which needle 30 extends. A pair of infusion ports 32, 34 are formed in the angled side walls of sleeve 26 to form a pathway for infusing liquid. Ports 32, 34 are fixed in size and shape.

The embodiments shown in FIGS. 2 and 3 are taken from U.S. Pat. No. 5,084,009 and as discussed above, it appears that ports 32, 34 are formed along the flattened portion of sleeve 26 and are the only infusion paths present.

Referring now to FIG. 4, the numeral 36 identifies a prior art infusion sleeve having an interior fluid passageway 38 and a discharge port 40. Sleeve 36 is shown mounted to a phacoemulsification needle 42 formed as a hollow straight cylindrical needle body having an open needle mouth 44 communicating with an internal aspiration passageway 46. It should be noted that sleeve flow path 38 actually comprises an annular space between the inner surface of sleeve 36 and the outer surface of needle 42.

Figure 5:
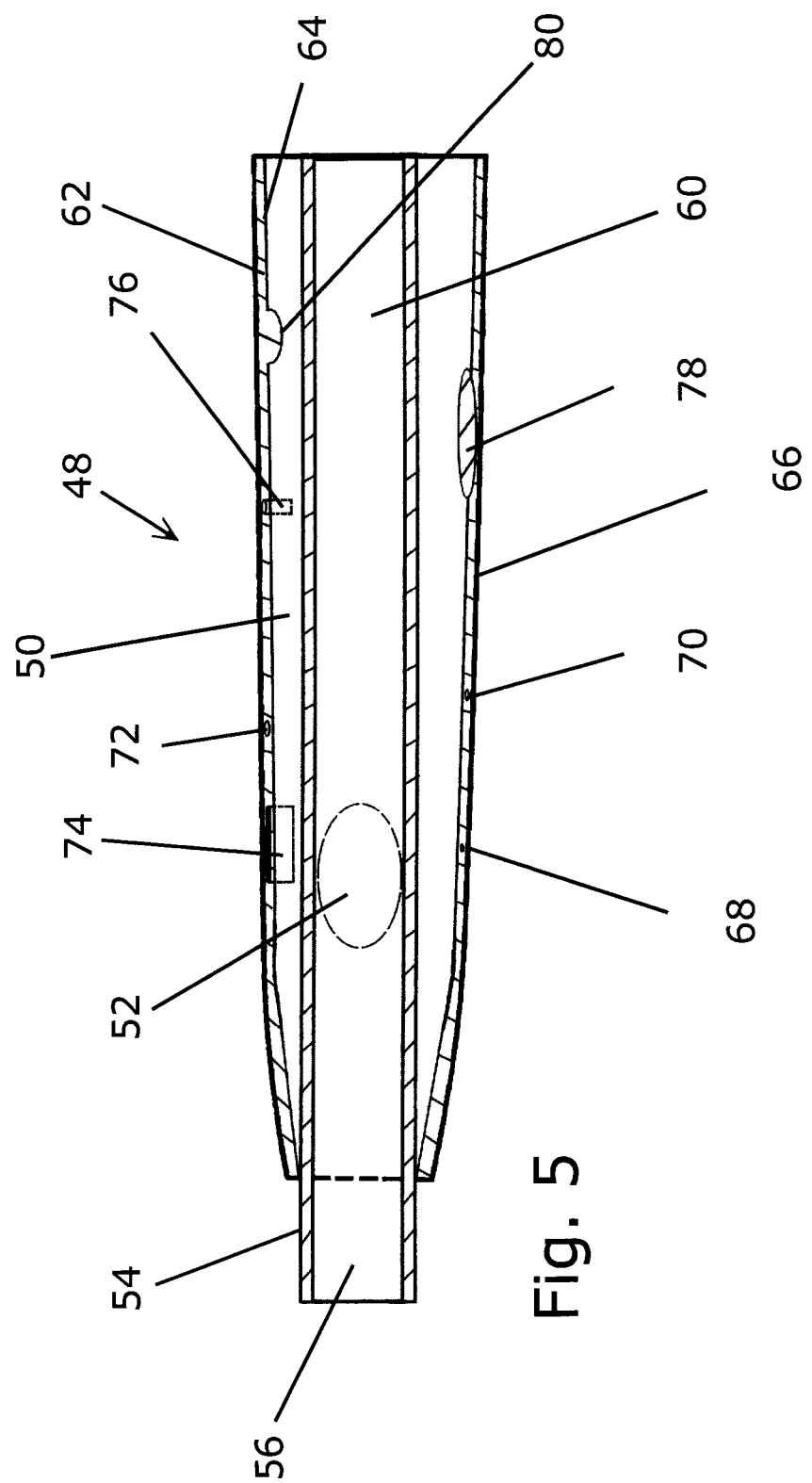
FIG. 5 is a lateral sectional view of an infusion sleeve embodying certain principles of the present invention.

Referring now to FIG. 5, an infusion sleeve 48 having a hollow tubular body is shown having a liquid pathway, passageway, or an inner fluid passageway 50 and a discharge port 52. Sleeve 48 is shown mounted to a phacoemulsification needle 54 having an open mouth 56 and a longitudinally extending internal aspiration passageway 60. The sleeve 48 and an outer surface of the needle 54 define the passageway 50, allowing irrigating liquid to pass into the sleeve 48 when the sleeve 48 is mounted to the handpiece (not illustrated).

It should be understood that needle 54 is exemplary of the general characteristics of phacoemulsification needles, that is, needles that are hollow, having an aspiration port communicating with an internal aspiration passageway. It is to be understood that such phacoemulsification needles are manufactured and provided in a variety of sizes, shapes, configurations and constructions and the principles of the present invention are applicable to all such constructions.

Sleeve 48 has an outer surface 62, and an inner surface 64. Inner and outer surfaces 62, 64 define therebetween a sleeve wall 66. In a first embodiment of the present invention, a weight 68 is embedded within sleeve wall 66 to provide a discontinuity in a mass distribution in the construction of sleeve 48. As can be seen in FIG. 5, weights that project beyond either the outer surface 62 or inner surface 64 of the sleeve 48 may generally be characterized as projections. As can further be seen in FIGS. 5 and 6, such weights and projections may be located asymmetrically on the sleeve wall 66. It should be understood that a number of such weights such as 70 and 72 may be distributed throughout sleeve 48 at selected locations to give sleeve 48 a desired degree of imbalance or eccentricity when it comes to mass distribution. Weights 68, 70, and 72 are shown as individual beads or inserts and may be formed from metal such as titanium or other material desirably having a specific gravity differing from the material from which sleeve 48 is manufactured.

In a second embodiment, a projection or weight 74 is embedded in wall 66 and has a generally arcuate rectangular shape and may extend about a portion of the inner periphery of wall 66. As can be seen in FIG. 5, at least a portion of the weight 74 extends outwardly beyond or above the inner surface 64 of the sleeve 48. As can further be seen in FIG. 5, weight 74 longitudinally extends along the tubular body of the sleeve 48 a distance that is substantially shorter than a longitudinal length of the sleeve tubular body.

In yet another embodiment, another projection or wire-like weight 76 is embedded in the wall 66 and extends about a portion of the periphery of sleeve 48. As can be seen in Fiq. 5, at least a portion of the wire-like weight 76 extends outwardly beyond or above the inner surface 64 of the sleeve 48. As can further be seen in FIG. 5, wire-like weight 76 longitudinally extends along the tubular body of the sleeve 48 a distance that is substantially shorter than a longitudinal length of the sleeve tubular body.

In another embodiment, another projection or internal weight 78 is attached to inner wall 64 or is set into wall 66. As can be seen in FIG. 5, at least a portion of the internal weight 78 extends outwardly beyond or above the inner surface 64 of the sleeve 48. As can further be seen in FIG. 5, internal weight 78 longitudinally extends along the tubular body of the sleeve 48 a distance that is substantially shorter than a longitudinal length of the sleeve tubular body.

In another embodiment, another projection or dimple 80 is formed as a portion of wall 66 and extends inwardly into passageway 50 and provides a point of non-uniform mass distribution even though dimple 80 is formed from the same material as sleeve 48. As can be seen in FIG. 5, at least a portion of the dimple 80 extends outwardly beyond or above the inner surface 64 of the sleeve 48. As can further be seen in FIG. 5, dimple 80 longitudinally extends along the tubular body of the sleeve 48 a distance that is substantially shorter than a longitudinal length of the sleeve tubular body.

Figure 6:
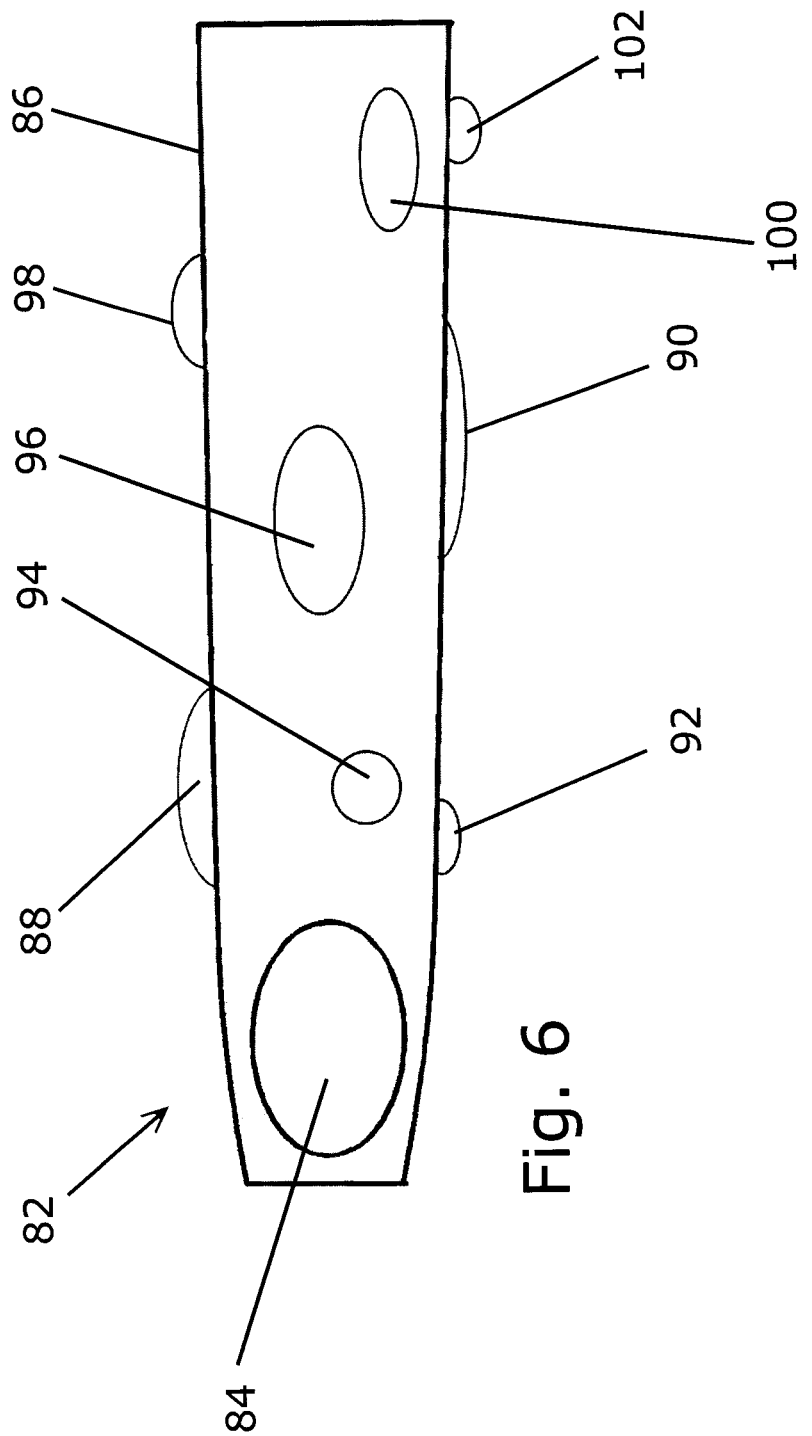
FIG. 6 is a lateral elevation of an infusion sleeve embodying certain principles of the present invention.

Referring now to FIG. 6, the numeral 82 identifies a phacoemulsification sleeve having a discharge port 84 and an outer wall 86. As can be seen in FIG. 6, sleeve 82 has a hollow tubular body. A series of weights is shown formed on outer wall 86. Weights such as 88 and 90 are formed integrally with sleeve 82 and provide discontinuity of mass distribution even though they are the same material. Weights such as those shown at 92, 94, 96, 98, 100 and 102 are attached to outer wall 86 and may be manufactured from materials different from that of sleeve 82. As can be seen in FIG. 6, the weights 88, 90, 92, 98, and 102 may be characterized as projections wherein at least a portion of the weights extend outwardly beyond or above the outer wall 86 of the sleeve 82. As can further be seen in FIG. 6, each of weights 88, 90, 92, 98, and 102 longitudinally extends along the tubular body of the sleeve 82 a distance that is substantially shorter than a longitudinal length of the sleeve tubular body.

It should also be understood that a combination of internal and external weights or mass distribution discontinuities can be combined to provide a sleeve that exhibits the desired contribution of eccentric motion to a phacoemulsification needle during surgery.

What is claimed is:

1. An infusion sleeve for use with a phacoemulsification handpiece, the handpiece of the type having a hollow phacoemulsification needle attached to and extending from a handpiece body, the needle having an outer surface, the handpiece having a pathway through which irrigating liquid passes, said infusion sleeve of the type having a proximal end attached to the handpiece and a distal end through which a portion of the needle protrudes, said sleeve comprising:
    a hollow tubular body having an outer surface and an inner surface defining therebetween a body wall;
    said sleeve adapted to enclose the needle outer surface to define a passageway for communicating with the liquid pathway to allow the liquid to pass into and through said sleeve when said sleeve is mounted to the handpiece; and
    said sleeve body wall comprising one or more projections positioned asymmetrically on said body wall for causing eccentric motion of the phacoemulsification needle, each such projection having at least one portion extending above one of said inner or outer surface of said tubular body, and
    each such projection longitudinally extending along said tubular body a distance that is substantially shorter than a longitudinal length of said tubular body.

2. The infusion sleeve as recited in claim 1 wherein at least one of said projections is formed with said sleeve as a single piece.

3. The infusion sleeve as recited in claim 1 wherein at least one of said projections is manufactured from a material different than that of said body wall.

4. The infusion sleeve as recited in claim 1 wherein at least one of said projections is an insert positioned in said body wall,
    said insert made from a material different than said body wall.

5. The infusion sleeve as recited in claim 4 wherein said insert is a segment of wire.

6. An infusion sleeve for use with a phacoemulsification handpiece, the handpiece of the type having a hollow phacoemulsification needle attached to and extending from a handpiece body, the needle having an outer surface, the handpiece having a pathway through which irrigating liquid passes, said infusion sleeve of the type having a proximal end attached to the handpiece and a distal end through which a portion of the needle protrudes, said sleeve comprising:
    a hollow tubular body having an outer surface and an inner surface defining therebetween a body wall; and
    said sleeve wall comprising at least one weight, said at least one weight positioned asymmetrically on said body wall for causing eccentric motion of the phacoemulsification needle, and said at least one weight longitudinally extending along said tubular body a distance that is substantially shorter than a longitudinal length of said tubular body.

7. The infusion sleeve as recited in claim 6 wherein said at least one weight is embedded within said sleeve.

8. The infusion sleeve as recited in claim 6 wherein said at least one weight is manufactured from a material different than that of said body wall.

9. The infusion sleeve as recited in claim 6 wherein said at least one weight is an insert positioned in said body wall,
    said insert made from a material different than said body wall.

* * * * *